United States Patent [19]
Chin

[11] Patent Number: 4,640,270
[45] Date of Patent: Feb. 3, 1987

[54] MALE ORGAN JACKET

[76] Inventor: Te-Chien Chin, 705 Windsor, Hercules, Calif. 94547

[21] Appl. No.: 731,042

[22] Filed: May 6, 1985

[51] Int. Cl.$^4$ .............................................. A61F 5/41
[52] U.S. Cl. ...................................................... 128/79
[58] Field of Search ................... 128/79; 604/346, 347

[56] References Cited

U.S. PATENT DOCUMENTS

| | | | |
|---|---|---|---|
| 4,022,196 | 5/1977 | Clinton | 128/79 |
| 4,381,000 | 4/1983 | Duncan | 128/79 |
| 4,429,689 | 2/1984 | Yanong | 128/79 |
| 4,488,541 | 12/1984 | Garcia | 128/79 |

FOREIGN PATENT DOCUMENTS

| | | | |
|---|---|---|---|
| 523141 | 6/1929 | Fed. Rep. of Germany | 128/79 |
| 1380425 | 1/1975 | United Kingdom | 128/79 |

Primary Examiner—Gene Mancene
Assistant Examiner—Cary E. Stone

[57] ABSTRACT

Disclosed is a sex aid device for supporting and/or strengthening the penis, especially the imperfect ones, comprising a semi-rigid three-sectioned casing of adjustable length. The sections of the casing are optional except the base section. A supporting strap with various connecting means connects the casing to the male body at different angles.

4 Claims, 10 Drawing Figures

U.S. Patent   Feb. 3, 1987   4,640,270
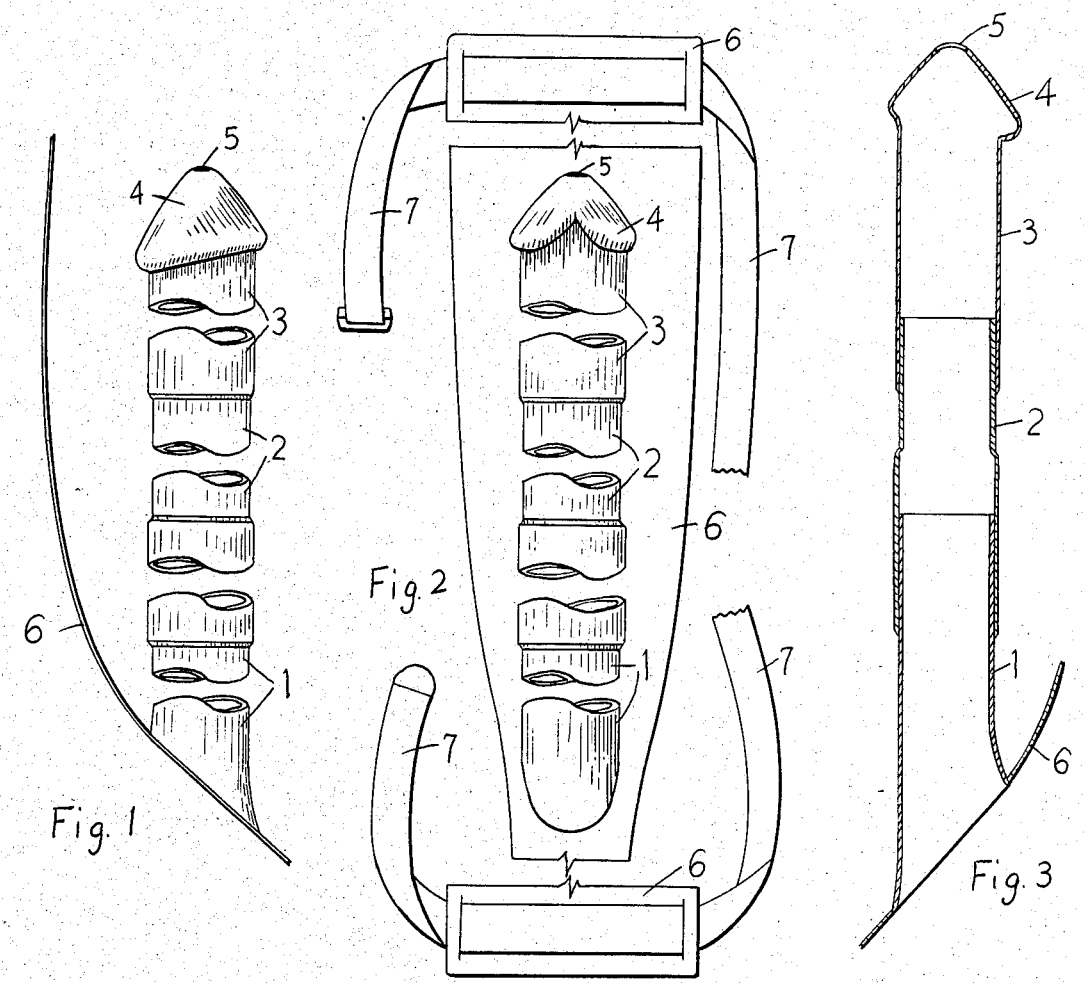
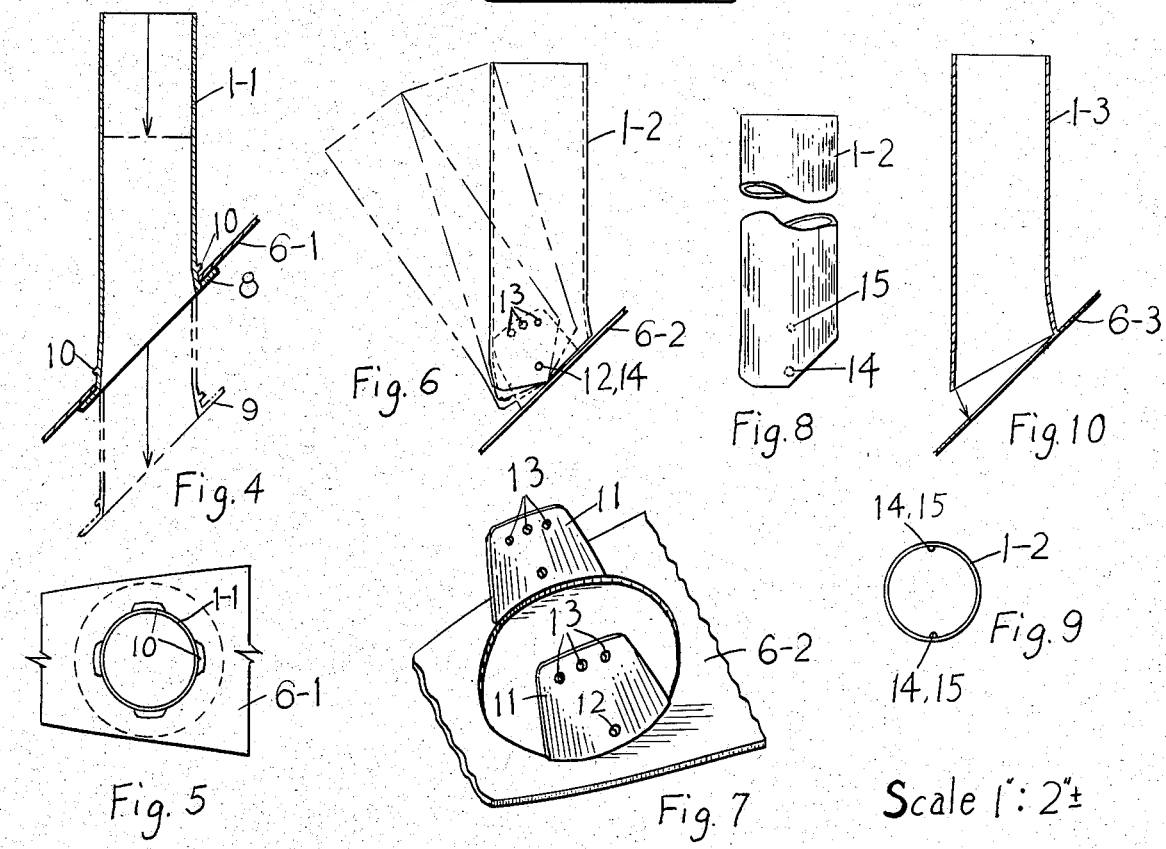
Scale 1":2"±

MALE ORGAN JACKET

BACKGROUND OF THE INVENTION

1. Field of the Invention

This invention relates generally to sex aid device, and particularly to an artificial supporter and supplement for the male organ to maintain harmonious married life.

2. Description of the Prior Art

Sexual harmony plays an important role in the maintenance of happy marriage. Unfortunately, many husbands will sooner or later find that their male organs are inadequate or unable to satisfy their wives because the male organs are easy to contract and become weaker owing to aging, sickness, injuries, hard work, excessive sexual activities, psychological factors, etc. while their partners' female organs become loose due to childbirth and long years of sexual activity.

To solve such problems, a number of devices have been proposed in the past. U.S. Pat. Nos. 4,022,196; 4,429,689; 4,488,541; 4,381,000; British Pat. No. 1,380,425 and German Pat. No. 523,141 illustrate some different approaches to these problems.

U.S. Pat. No. 4,022,196 illustrates one embodiment including a relatively rigid base to support the apparatus against the male body and into which fits a penis for enhancing sexual relations with the female.

U.S. Pat. No. 4,429,689 discloses a device comprising a tubular member being adapted to extend from the base of a penis to the glans penis with upper and lower longitudinally extending flexible supports and elastic flexible sides. The bottom support is a spoonlike member for receiving the bottom of the glans penis. The device preferably has upper and lower transverse ridges.

U.S. Pat. No. 4,488,541 describes a sex aid adapter including a flexible pubic shield with a plurality of monolithically formed inverted conical projections.

U.S. Pat. No. 4,381,000 shows a device comprising a sheath encircling a penis from the base to a point just behind the glans to shield the same from contact with the female organ so as to delay ejaculation.

A problem in the prior art is in providing the sex aid with more suitable angles for facilitating insertion and copulation. We must understand that almost all male organs and female organs are not exactly the same in size, form, position of the organ and position needed at different stages of copulation.

Another problem in the prior art is the length of the sex aid devices, which would be obviously more desirable if their length can be adjusted at will to satisfy the different needs at different time.

The third problems is that the sex aid device can be more useful if it can be used either in part or in whole. For instance, one may need only the base portion of it to support an impotent or a half-erected penis to work but leave the glans penis exposed, another may use the whole sheath to support or strengthen a weak or undersized or early ejaculating penis.

The present invention can solve all these problems because the sections of the jacket or casing are separable and one or more of them can be omitted in use, and the overlapping portions of the sections can be adjusted to desired length at will, and the strap holding the jacket can furnish various angles to the jacket.

SUMMARY OF THE INVENTION

The device disclosed and claimed herein comprises three separable sections, each of which are optional except the base section, a penis-like casing of adjustable length, and a supporting strap for fastening the said casing to a male body at several angles.

The objects of the present invention are:

To provide a new and efficient prosthetic penile device which can either delay or avoid ejaculation; support impotent male organ or make up undersized penis;

To provide a versatile male organ casing with separable sections to meet the different needs of different people on different occasions.

To provide a versatile male organ jacket which can be attached to any human body at several angles;

To provide stability and strengthen the wedlock in many families in which inharmonious sexual relations may become a serious factor between the husband and the wife;

To make up for the deficiencies on many men who cannot successfully satisfy their wives' sexual needs.

BRIEF DESCRIPTION OF THE DRAWINGS

FIG. 1 is a broken side view of the present invention, the Male Organ Jacket (MOJ).

FIG. 2 is a broken elevation view of the device on a broken strap.

FIG. 3 is a side sectional view of the MOJ with a part of its strap.

FIG. 4 is a side sectional view of the base section of the MOJ with a portion of another type of strap. The lower part of this figure shows that the base section of the MOJ can move through the strap.

FIG. 5 is a top view of FIG. 4.

FIG. 6 is a side view of the base section of the MOJ on a portion of another type of strap. Two phantom lined base sections of the MOJ shows its different positions.

FIG. 7 is an enlarged perspective view of a portion of the strap with two supporting walls as seen in FIG. 6.

FIG. 8 is a broken side view of the base section of the MOJ as shown in FIG. 6.

FIG. 9 is a top view of FIG. 8.

FIG. 10 is a side sectional view of another type of base section of the MOJ with a portion of another type of strap.

DESCRIPTION OF THE PREFERRED EMBODIMENTS

FIG. 1 is a broken side view of the present invention, the Male Organ Jacket, comprising the base section 1, the extension section 2 and the top section 3 which has a glans-like portion 4, all made of suitable semi-rigid, resiliently flexible material. There may be a hole 5 in the tip of 4. A portion of the strap 6 is seen here to support the apparatus.

FIG. 2 shows almost the whole device except that both the MOJ and its strap 6 and 7 are shown in broken figures. These three sections of the MOJ are put together by overlapping a portion of the sections, which condition can be seen more clearly in FIG. 3, and, therefore, they can be disconnected easily to meet the different users' different needs. For instance, the user may use only the base section 1 with the strap 6, or the base section 1 plus the extension section 2 with the strap 6, or the base section 1 plus the top section 3 with strap 6, or all three sections wth strap 6. The strap 6 and 7 is used to support the MOJ and in turn to fasten the whole device to the male body.

FIG. 3 is a side sectional view of the MOJ on a portion of the strap 6. The overlapping part of the three sections 1, 2 and 3 can be increased or decreased at will.

FIG. 4 shows the side sectional view of an alternative base section 1-1 of the present invention on a portion of an alternative strap 6-1. A rim 8 is at the bottom of this type of base section and there are some button-like small projections 10 near to the lower end of the outside wall of the base section 1-1.

FIG. 5 is a top view of FIG. 4.

FIG. 6 shows an alternative type of base section 1-2 of the device. This type of base section can be transposed in different positions by sliding the pivotal buttons (one on each side inside the base section 1-2) into the opposite holes 12 and inserting two buttons 15 (also inside 1-2) into any pair of the holes 13. The strap 6-2 is suitable for accommodating this type of base section 1-2.

FIG. 7 is an enlarged perspective view of a portion of the strap 6-2 with two small walls 11 each having a hole 12 and some small holes 13.

FIG. 8 illustrates a broken side view of the base section 1-2 as seen in FIG. 6. There are two small buttons 14 and 15 on opposite sides inside the wall of the base section 1-2.

FIG. 9 is a top view of FIG. 8. There are two small buttons 14 and 15 on each side of the inside wall of base section 1-2.

FIG. 10 is a side sectional view of another type of base section 1-3 on a portion of another type strap 6-3 showing only a small portion of the base section 1-3 to be connected to strap 6-3 while the most portion of it is separate from the strap 6-3 for freer movement.

What is claimed is:

1. A penile prosthetic device comprising, in combination: base means, including a tubular base section adapted to hold and support a base portion of a penis shaft and a supporting strap, said tubular base section being securely connected to said strap, which in turn may be securely fastened to a lower abdominal area of a male body; extension means comprising a tubular extension section having two ends, one end having a larger diameter than the other end, the larger end being able to hold any portion of the base section tightly whereas the smaller end being able to be inserted closely inside a lower end of a top section, wherein the ends overlap; and said top section having a tubular section and a glans-penis like top having a hole in its tip.

2. The device of claim 1 wherein the extension section and the top section are removable and may be used only when needed.

3. The device of claim 2 in which male users may choose to use the base section only, both the base and extension sections, both the base and top sections, or all of the sections.

4. The device of claim 1 wherein the length of the device may be adjusted by moving the overlapping ends of the sections together or away from one another.

* * * * *